United States Patent [19]
Yoon

[11] Patent Number: 5,632,717
[45] Date of Patent: May 27, 1997

[54] PENETRATING ENDOSCOPE

[76] Inventor: InBae Yoon, 2101 Highland Ridge Dr., Phoenix, Md. 21131

[21] Appl. No.: 368,215

[22] Filed: Jan. 3, 1995

Related U.S. Application Data

[63] Continuation-in-part of Ser. No. 320,192, Oct. 7, 1994, abandoned.

[51] Int. Cl.[6] ...................................................... A61B 1/00
[52] U.S. Cl. ........................ 600/106; 600/104; 600/127; 600/129; 600/130
[58] Field of Search ............................. 600/104, 105, 600/106, 117, 127, 129, 115, 130, 138, 137; 606/170, 171

[56] References Cited

U.S. PATENT DOCUMENTS

| | | |
|---|---|---|
| 4,254,762 | 3/1981 | Yoon . |
| 4,319,563 | 3/1982 | Kubota . |
| 4,361,139 | 11/1982 | Takagi ................................ 600/138 |
| 4,625,713 | 12/1986 | Hiraoka .............................. 600/104 |
| 4,793,326 | 12/1988 | Shishido ................................. 128/4 |
| 4,950,278 | 8/1990 | Sachse et al. .................... 600/104 X |
| 4,984,563 | 1/1991 | Renaud ............................ 600/106 X |
| 5,027,792 | 7/1991 | Meyer ................................. 600/104 |
| 5,271,380 | 12/1993 | Riek et al. . |
| 5,372,588 | 12/1994 | Farley et al. . |
| 5,376,076 | 12/1994 | Kaali . |
| 5,380,291 | 1/1995 | Kaali . |
| 5,385,572 | 1/1995 | Nobles et al. . |
| 5,441,041 | 8/1995 | Sauer et al. ...................... 600/106 X |
| 5,445,142 | 8/1995 | Hassler, Jr. . |

OTHER PUBLICATIONS

United States Surgical Corp., "Visiport" Disposable Optical Trocar, Jul., 1994.
"Optiview" Brochure, Ethicon Endo–Surgery, one page 1994.

Primary Examiner—Richard J. Apley
Assistant Examiner—Beverly M. Flanagan

[57] ABSTRACT

An endoscope includes an endoscope tube, illumination and viewing systems disposed within the endoscope tube in a manner to define a blunt distal end, and a penetrating member coupled with an operating mechanism for moving the penetrating member between a retracted position where a distal end of the penetrating member is proximally spaced from the blunt distal end of the endoscope and an extended position where the distal end of the penetrating member protrudes beyond the blunt distal end of the endoscope. The penetrating member can be a blade, one or more needles or any other type of instrument suitable for penetrating anatomical tissue. Upon being extended, the penetrating member can be held in the extended position, automatically retracted and/or reciprocatingly moved as desired.

29 Claims, 9 Drawing Sheets

PENETRATING ENDOSCOPE

CROSS-REFERENCE TO RELATED APPLICATIONS

This application is a continuation-in-part of application Ser. No. 08/320,192, filed Oct. 7, 1994, now abandoned, the disclosure of which is incorporated herein by reference.

BACKGROUND OF THE INVENTION

1. Field of the Invention

The present invention pertains to endoscopes in general and, more particularly, to an endoscope with a penetrating member for penetrating into anatomical tissue.

2. Discussion of the Prior Art

Endoscopic and minimally invasive procedures have become widely accepted for surgery and diagnosis due to the associated advantages relating to reduced trauma and hospitalization time. However, the performance of an endoscopic procedure usually requires that the surgeon be able to view inside the body through a small opening or incision created in the anatomical tissue. Typically, the openings are created using a penetrating instrument including an obturator, such as a trocar, disposed within a cannula or sleeve. The obturator has a sharp tip that is pressed against the anatomical tissue to penetrate through the anatomical tissue, after which the obturator is withdrawn leaving the cannula in place to form a portal. An apparatus known as an endoscope can then be inserted through the cannula for accomplishing the functions of illuminating and viewing inside the body.

While prior art endoscopes are widely used, they suffer from many disadvantages when used in the procedures for which they are presently recommended. A major disadvantage of prior art endoscopes is that they cannot be used during penetration of anatomical tissue to view the anatomical tissue being penetrated. Thus, it is difficult for a surgeon to know whether to alter the path of the penetrating member to avoid blood vessels and other types of anatomical tissue and organs.

SUMMARY OF THE INVENTION

Accordingly, it is a primary object of the present invention to overcome the above-mentioned disadvantages of the prior art and to provide an endoscope that can be used during penetration of anatomical tissue for viewing the anatomical tissue being penetrated.

Another object of the present invention is to more accurately locate an endoscope within a body using a penetrating member extended from a distal end of the endoscope to penetrate anatomical tissue.

Yet another object of the present invention is to access potential spaces between layered or adjacent tissue structures, non-existing spaces in homogenous tissue, and existing spaces, such as anatomical cavities, by use of a penetrating member extended from an endoscope.

Still another object of the present invention is to carry a retractable penetrating member at the distal end of an endoscope for penetrating into anatomical tissue when extended and permitting non-traumatic contact between the endoscope and anatomical tissue when retracted.

It is another object of the present invention to automatically retract a penetrating member carried at a distal end of an endoscope when the penetrating member has extended a predetermined distance.

Yet another object of the present invention is to initiate reciprocating movement of a penetrating member between a retracted position within an endoscope and an extended position protruding from a distal end of the endoscope.

A further object of the present invention is to control penetration of an endoscope through anatomical tissue by extending needles from a distal end of the endoscope to perforate the tissue and advancing the endoscope against the perforated tissue.

Some of the advantages of the present invention over the prior art are that the endoscope can be used to view anatomical tissue as it is penetrated, that cutting or penetrating of anatomical tissue can be accomplished with or without pushing the endoscope against the tissue, that the path of penetration of the endoscope can be altered to avoid blood vessels and other anatomical tissue and organs that are viewed during penetration, that the endoscope can be positioned within potential, non-existing or existing spaces, that a penetrating member can be withdrawn or retracted into the endoscope leaving a relatively smooth, rounded distal end for manipulating tissue, and that instruments can be passed through the endoscope to perform functions such as cutting or dissecting tissue within the body.

The present invention is generally characterized in an endoscope including an endoscope tube, illumination and viewing systems disposed within the endoscope tube in a manner to define a blunt distal end, and a penetrating member disposed at least partly within the endoscope tube and having a distal end for penetrating anatomical tissue, the penetrating member being coupled with an operating mechanism for moving the penetrating member between a retracted position where the distal end of the penetrating member is proximally spaced from the blunt distal end of the endoscope and an extended position where the distal end of the penetrating member protrudes beyond the blunt distal end of the endoscope. The penetrating member can be a blade with one or more cutting edges and/or teeth, one or more needles with penetrating tips, a rotary cutter with burrs or any other type of instrument suitable for penetrating anatomical tissue. Furthermore, the operating mechanism can be configured to pivot or linearly translate the penetrating member between the retracted and extended positions, to automatically retract and/or reciprocate the penetrating member and/or to rotate the penetrating member about a longitudinal axis of the endoscope. The endoscope can also be formed of separate illuminating and viewing units to facilitate disposal of one unit and reuse of the other as desired.

Another aspect of the present invention is generally characterized in a method of penetrating anatomical tissue including the steps of positioning a blunt distal end of an endoscope proximate the anatomical tissue, extending a penetrating member from a retracted position within the endoscope to an extended position protruding from the blunt distal end of the endoscope, penetrating into the anatomical tissue with the penetrating member, and advancing the endoscope into the penetrated tissue. The penetrating member can also be retracted prior to, during or after the endoscope has been advanced into the penetrated tissue. Further, needles can be extended as part of the extending step to perforate the anatomical tissue prior to advancing the endoscope.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIGS. 18A–21A are fragmentary side views illustrating operation of an automatic retracting mechanism for the endoscope of the present invention.

FIGS. 18B–21B are rear views illustrating operation of the automatic retracting mechanism shown in FIGS. 18A–21A.

DESCRIPTION OF THE PREFERRED EMBODIMENTS

Figures 1, 2, 3:
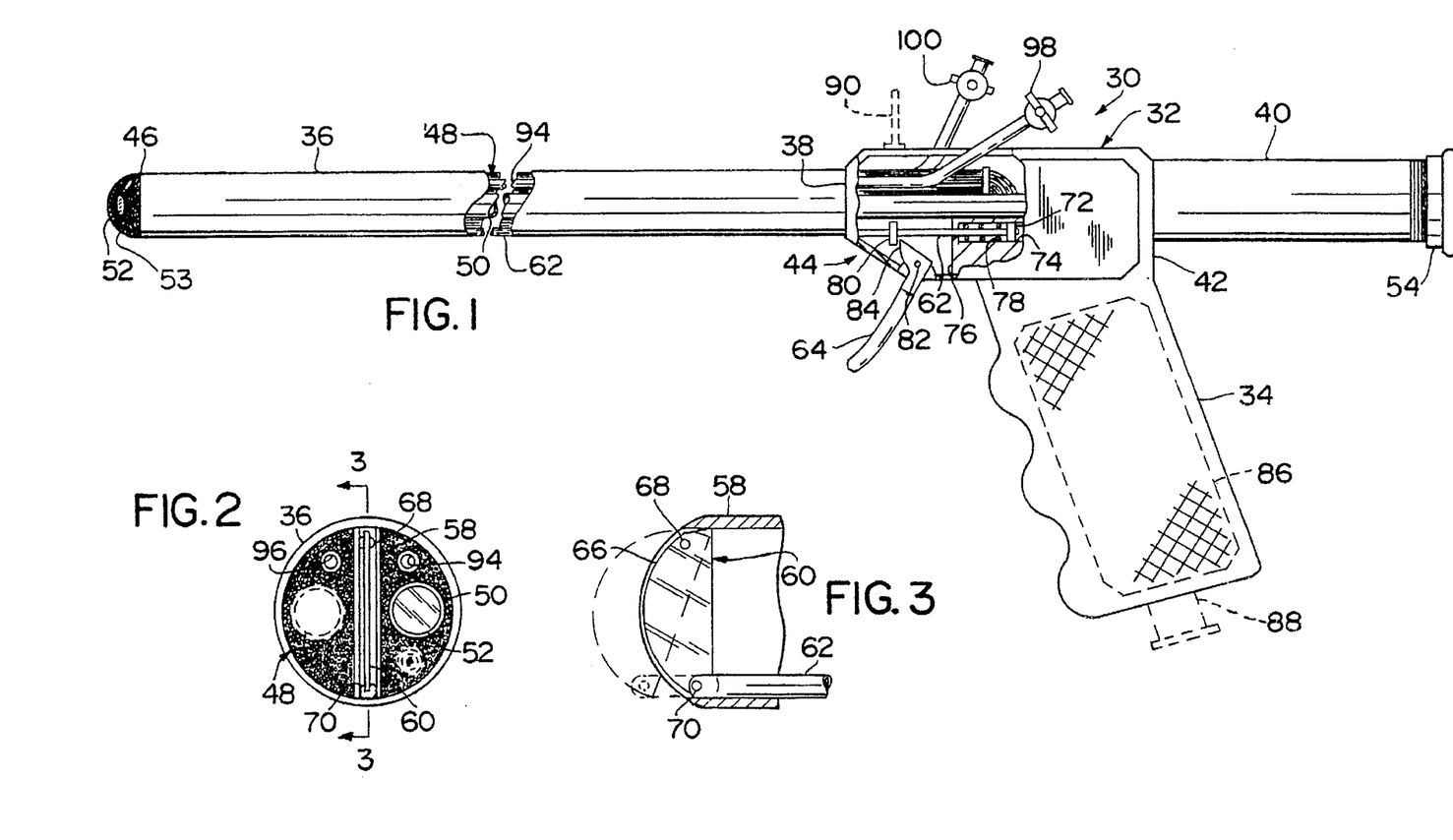
FIG. 1 is a broken side view, partly in section, of an endoscope according to the present invention.
FIG. 2 is a front view of the endoscope of FIG. 1.
FIG. 3 is a cross-sectional view taken along line 3—3 in FIG. 2.

An endoscope 30 according to the present invention, as illustrated in FIGS. 1–3, includes a housing 32 with a handle 34, an endoscope tube 36 extending distally from a front wall 38 of the housing, a viewing port 40 extending proximally from a rear wall 42 of the housing and a penetrating mechanism 44 disposed within the housing and endoscope tube for operating a blade or other type of penetrating member disposed at the distal end 46 of the endoscope tube 36.

Endoscope tube 36 is a rigid or flexible elongate cylinder enclosing a conventional optical system including an illumination transmission system utilizing light conducting optical fibers 48 and a viewing system having an optical channel 50 of generally cylindrical configuration containing conventional object and relay lens assemblies (not shown). Optical channel 50 extends lengthwise through endoscope tube 36 along an eccentric longitudinal axis of the tube and terminates distally at an optical window 52. Optical fibers 48 surround the optical channel 50 and protrude from the distal end 46 of the tube forming a blunt, relatively smooth, hemispherical surface 53 at the distal end of the endoscope around the optical channel 50. A similar optical system is shown and described in U.S. Pat. No. 4,319,563 to Kubota, the disclosure of which is incorporated herein by reference; and, accordingly, the optical system will not be described in great detail herein.

Proximal viewing port 40 is also conventional and includes an imaging lens assembly (not shown) for focusing the image received by the relay lens assembly of optical channel 50. The viewing port 40 is configured to be coupled with an eye piece 54 as shown and/or any other type of imaging system, including those utilizing detectors and processing units for creating television displays on a cathode ray tube.

The penetrating mechanism 44 includes a tubular penetrating channel 58 of generally rectangular cross-section disposed within the endoscope tube 36, a blade 60 mounted within the channel 58 near an open distal end of the channel, a control rod 62 pivotally connected to the blade 60 and extending proximally into housing 32, and a trigger 64 for engaging the rod 62 to move the blade 60 distally. The penetrating channel 58 is diametrically disposed within the endoscope tube 36 along a central longitudinal axis of the tube and defines an opening at the distal end of the tube for passage of the blade 60. Blade 60 is flat with a semicircular or curved cutting edge 66 facing distally and is pivotally mounted on a pin 68 secured to a wall or walls of the channel 58. A distal end of rod 62 is flattened or slotted and is pivotally connected to blade 60 by a pin 70 at a location diametrically opposed from pin 68 so that distal movement of the rod will induce rotation of the blade about pin 68 as shown in phantom in FIG. 3. It will be appreciated that rotation of blade 60 about pin 68 causes cutting edge 66 to protrude distally from channel 58.

A proximal end of rod 62 carries or forms a round flange 72 disposed within a cylindrical chamber 74 defined by a mounting structure 76 in housing 32. A bias member 78 in the form of a helical coil spring is disposed around the rod 62 and is mounted in compression between flange 72 and a wall 79 at the distal end of chamber 74 to bias the rod in a proximal direction. A second round flange 80 is carried or formed on the rod 62 intermediate the mounting structure 76 and housing front wall 38. Trigger 64 extends at an angle from housing 32 and is distally spaced from handle 34. The trigger 64 is mounted on a pin 82 secured to the housing and includes a distally-angled protrusion or hammer 84 extending toward flange 80 on rod 62. A torsion spring or some other bias member (not shown) is connected between the trigger 64 and housing 32 to bias the trigger clockwise toward a rest position, shown in FIG. 1, where the distally-angled protrusion 84 is proximally spaced from flange 80. Handle 34 resembles a pistol grip and is configured to accommodate a portable battery-operated light source, shown in phantom at 86 in FIG. 1, or an illumination coupling port, shown in phantom at 88 in FIG. 1, for connection with a remote light source. An electrical connector is also shown in phantom at 90 in FIG. 1 for performing unipolar or bipolar electrical cutting procedures, for example utilizing the blade 60 of the endoscope 30 and conventional insulating techniques. In a preferred embodiment, the distal protrusion 84 of the trigger serves as a conductive element so that blade 60 will only be conducting when trigger 64 contacts the control rod flange 80.

A pair of tubular passages 94 and 96 extend alongside the cutting channel 58 on opposite sides of the channel and define openings at the distal end 46 of the endoscope tube 36. Proximal ends of the passages 94 and 96 extend at an angle from housing 32 toward a proximal end of the endoscope 30 and are coupled with stopcock valves 98 and 100, respectively, for controlling passage of fluids, anatomical tissue and medical instruments through the passages. Passages 94 and 96 can thus be used alone or in combination for creating suction at the distal end of the endoscope 30, injecting fluids such as lens cleaning solution, insufflating, aspirating and/or performing any other procedure involving transmission or collection of fluids, collection of small tissue samples, and/or manipulation of instruments to cut, cauterize, suture or perform other medical functions.

In use, the endoscope 30 can be positioned externally of the body or can be located within anatomical tissue or an anatomical cavity by passage of the endoscope tube 36 through an existing opening or endoscopic portal. If the endoscope tube 36 is positioned within anatomical tissue or an anatomical cavity, the illuminating and imaging systems previously described can be used in the conventional manner to navigate through the tissue or cavity and to locate anatomical tissue which is to be cut, penetrated or dissected, for example. Once located, the endoscope can be moved to a position proximate the anatomical tissue of interest. With the endoscope tube 36 positioned adjacent the anatomical tissue, the penetrating mechanism 44 can be employed for cutting into or penetrating the anatomical tissue with or without exerting any distal pressure on the tissue by movement of the distal end of the endoscope 30 against the tissue.

Prior to operating the penetrating mechanism 44, blade 60 is held within the penetrating channel 58 in a retracted position as a result of the control rod 62 being biased proximally by spring 78. In the retracted position, shown by solid lines in FIG. 3, the arcuate cutting edge 66 conforms approximately to the hemispherical shape of the distal end 53 of the endoscope formed by the fiber optic members 48 protruding from the endoscope tube 36. As mentioned previously, trigger 64 is normally biased clockwise such that the distally-angled protrusion 84 is normally spaced proximally of flange 80 on control rod 62.

With the distal end 53 of the endoscope 30 positioned against or near anatomical tissue, cutting is commenced by pulling trigger 64 toward handle 34 to rotate the trigger in a counterclockwise direction looking at FIG. 1. Counterclockwise rotation of the trigger 64 moves the distally-angled protrusion 84 into contact with flange 80 on control rod 62 urging the rod in a distal direction against the proximal bias of spring 78.

As best seen in FIG. 3, distal movement of the control rod 62 causes blade 60 to rotate or pivot clockwise about pin 68. Rotation of the blade 60 causes the cutting edge 66 to protrude distally from the penetrating channel 58 and to thereby cut into the anatomical tissue. If the handle 34 is not moved, a linear cut can be made having a length approximately equal to the inside diameter of the cutting channel 58. At this point the blade 60 can be retracted back into the penetrating channel 58 by releasing the trigger 64, allowing spring 78 to move the control rod 62 in a proximal direction. Trigger 64 is biased to rotate in a clockwise direction, away from flange 80, into the rest position shown in FIG. 1.

The endoscope 30 can then be advanced incrementally through the anatomical tissue by repeatedly cutting and advancing the distal end 53 of the endoscope into the cuts. At any time during the procedure, the distal window 52 at the end of the optical channel 50 is positioned for viewing the tissue prior to, during and after a cut is made so that, for example, the direction of the endoscope can be adjusted to avoid certain vessels or areas of the body. Further, passages 94 and 96 can be used individually or together for passing fluids into the anatomical tissue or over the window 52, creating suction to collect fluids and small tissue samples, for aspiration or insufflation, for insertion of instruments into the body and for performing other functions requiring a passage from the proximal end of the endoscope into the body. Also, with blade 60 retracted, endoscope 30 can be manipulated within anatomical tissue or an anatomical cavity like an ordinary endoscope and in a conventional manner without fear of traumatically contacting the anatomical tissue because of the rounded configuration of the distal end 53.

As mentioned previously, when connector 90 is provided, an electrically conductive path can be formed between the connector and the blade 60 for performing unipolar or bipolar electrosurgical procedures. If trigger 64 and control rod 62 are utilized as conductive elements in the electrically conductive path, the blade will normally be non-conducting since the distally-angled protrusion 84 of the trigger is normally spaced from flange 80 on the control rod interrupting the conductive path. When the trigger 64 is pulled, however, the distally-angled protrusion 84 contacts flange 80 on the control rod 62 advancing the blade distally and simultaneously completing the electrical circuit. Electrical cutting or cautery is performed using the exposed blade as a conductor, and when the electrosurgical procedure is completed, trigger 64 is released to retract the blade 60 and to return the electrically conductive path to its normally open or interrupted condition.

Figure 4:
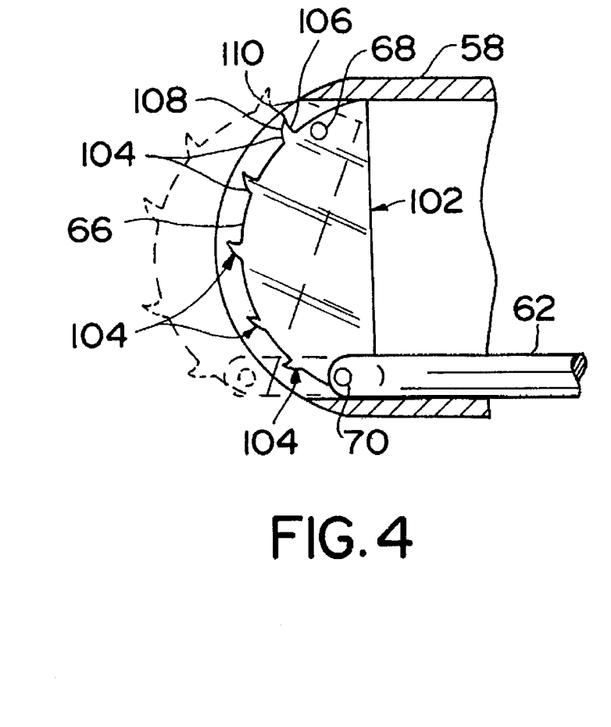
FIG. 4 is a side view of a modified blade for use with the endoscope of FIG. 1.

A modified blade for the endoscope 30 of the present invention is shown in FIG. 4. The modified blade 102 is similar to blade 60 but with a plurality of teeth 104 carried at spaced locations along the length of cutting edge 66. Teeth 104 are generally triangular with upwardly curved sides 106 and 108 converging at a sharp tip or point 110 radially spaced from cutting edge 66. Five teeth spaced at regular angular intervals are shown in FIG. 4; however, it will be appreciated that any number of teeth can be carried on the cutting edge of the blade at regular or irregular intervals. The spacing and size of the teeth are preferably chosen to facilitate penetration or perforation of tough anatomical tissue. The upward or clockwise curvature of the teeth assures that the tips of the teeth will be driven through the tissue when the blade is pivoted or rotated in a clockwise direction as shown in phantom in FIG. 4. When the blade is retracted, the tips 110 of the teeth are proximally spaced from the distal end of the endoscope and the penetrating channel 58, protecting the tips from inadvertent contact with anatomical tissue.

Figure 5:
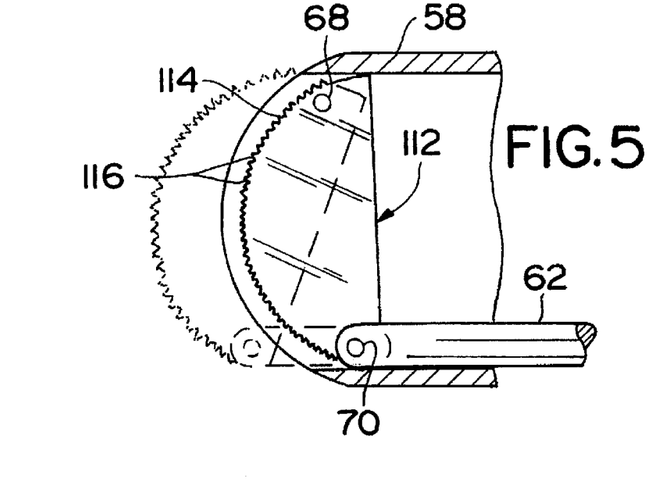
FIG. 5 is a side view of another modified blade for use with the endoscope of FIG. 1.

Another modified blade for use in the endoscope 30 of the present invention is shown in FIG. 5. The blade 112 is similar to blade 60 but with a serrated cutting edge 114. Cutting edge 114 is notched at regular angular intervals to form a plurality of closely spaced radial teeth 116. Teeth 116 can have any shape depending on the shape and size of the notch, including triangular, square, rectangular, polygonal or curved configurations. The close spacing of the teeth assures a smooth cut while facilitating penetration of tough tissue.

Figure 6:
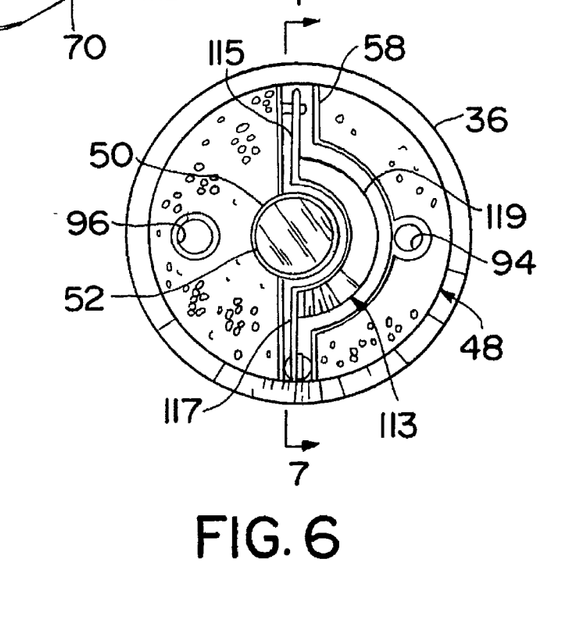
FIG. 6 is a front view of a modified endoscope according to the present invention.
Figure 7:
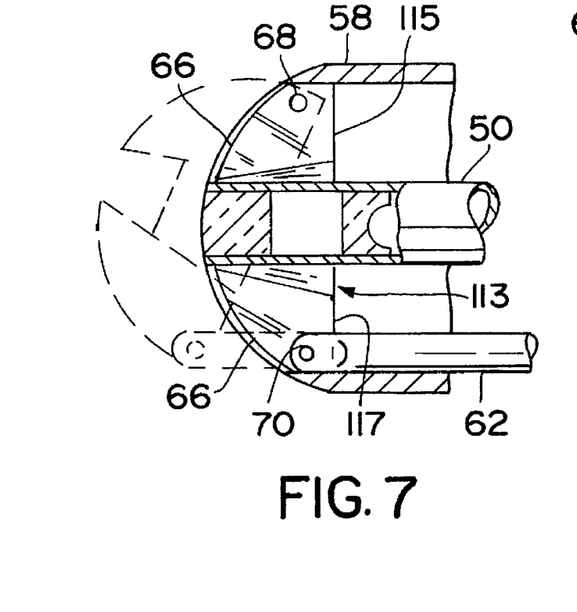
FIG. 7 is a side view, partly in section, of the modified endoscope of FIG. 6.
Figure 8:
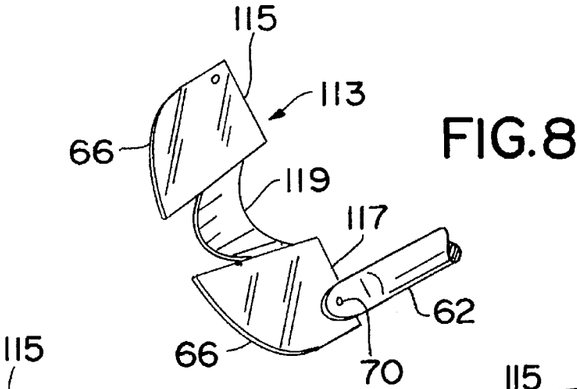
FIG. 8 is a detailed view in perspective of the penetrating member for use with the endoscope of FIG. 6.

A modification of the endoscope 30 of the present invention is shown in FIGS. 6-8 with the primary differences being the position of the optical channel 50 along a central longitudinal axis of the endoscope tube 36 and the configuration of the blade 113. The modified blade 113 is similar to the blade 60 previously described, but with two flat blade portions 115 and 117 connected by a rigid frustoconically shaped hinge or connecting portion 119. Penetrating channel 58 for the endoscope shown in FIG. 6 includes a pair of generally rectangular sections on opposite sides of the optical channel 50 for accommodating the flat blade portions 115 and 117 and a curved section to one side of the optical channel joining the rectangular sections and accommodating the frustoconically shaped connecting portion 119. The flat blade portion 115 shown at the top of FIG. 7 is pivotally mounted on a pin 68 secured to a wall or walls of the channel 58 with the lower flat blade portion 117 being connected to the control rod 62 by a pin 70. As best seen in FIGS. 6 and 7, the frustoconical connecting portion 119 of the blade wraps around the centrally disposed optical channel 50 while providing clearance for pivotal movement of the blade 113 about pin 68 such that the blade can be moved from the retracted position within the cutting channel 58 to an extended protruding position where the cutting edges 66 at the distal ends of the flat blade portions 115 and 117 protrude distally from the distal end of the endoscope and the penetrating channel 58, as shown in phantom in FIG. 7. Passages 94 and 96 are shown on opposite sides of the optical channel 50 within the hemispherical distal end 53 formed by the fiber optic fibers 48 but can be positioned as desired at the distal end of the endoscope. Use of the modified endoscope 30 proceeds essentially as previously described, with the exception that a substantially unobstructed view is provided by the centrally disposed optical channel 50 and that pivotal movement of the modified blade 113 in the manner previously described will result in a two-part cut being made by the upper and lower flat blade portions 115 and 117. For the blade shown, however, the two cuts made by the blade portions will be colinear and, depending on the amount of extension, can be made to intersect in order to form a single substantially linear cut.

Figures 9, 10, 11:
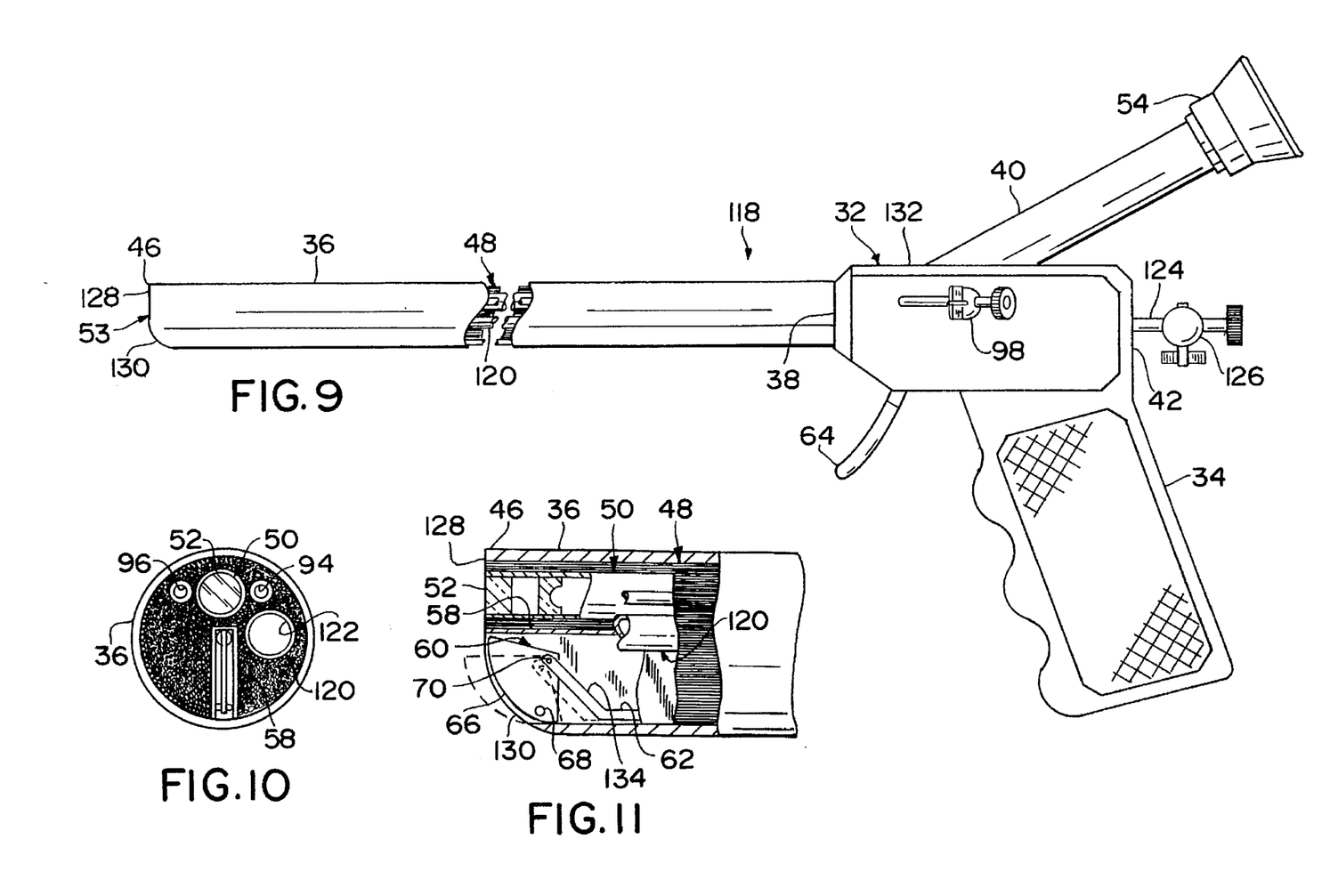
FIG. 9 is a broken side view of a modified endoscope according to the present invention.
FIG. 10 is a front view of the endoscope of FIG. 9.
FIG. 11 is a fragmentary side view, partly in section, of the distal end of the endoscope of FIG. 6.

The modified endoscope 118 illustrated in FIGS. 9-11 is similar to the endoscope 30 shown in FIG. 1 but is configured to accommodate an operating channel 120 for passing instruments and other objects and fluids through the endoscope. Operating channel 120 is a rigid or flexible cylinder that extends directly or straight through housing 32 and endoscope tube 36 of endoscope 118 to define an aperture 122 at the distal end 46 of the tube alongside the penetrating channel 58. A proximal end 124 of the operating channel 120 protrudes from the housing rear wall 42 and is coupled with a stopcock valve 126 to control passage of fluids, tissue and instruments through the operating channel.

The distal end 53 of the endoscope 118 is blunt and includes a flat upper portion 128 and a rounded lower portion 130 formed in part by the distal end 46 of endoscope tube 36. Penetrating channel 58 is similar to that shown in FIG. 1 but extends only partway across the endoscope tube 46 forming an opening along the rounded portion 130 of the distal end of the endoscope. Optical channel 50 is arranged above the penetrating channel 58 with optical window 52 disposed within the flat upper portion 128 of the distal end of the endoscope. As such, optical window 52 can be plano as shown. A proximal end of optical channel 50 is angled within housing 32 and extends through an upper wall 132 of the housing to mate with viewing port 40.

Referring now to FIG. 11, a wedge-shaped blade 60 is shown having a curved cutting edge 66 conforming to the shape of the rounded lower portion 130 of the endoscope distal end. The blade 60 is pivotally mounted on a pin 68 secured to a bottom of the penetrating channel 58 and control rod 62 is shown as having an upwardly angled arm 134 connecting with a pin 70 mounted on the blade 60 near a top edge of the blade in a manner to produce rotation of the blade 60 in a counterclockwise direction looking at FIG. 11 when the rod is advanced distally. As shown in phantom in FIG. 11, rotation of blade 60 about pin 68 advances the cutting edge 66 of the blade beyond the distal end of endoscope tube 36 without exposing the rod 62 or pin 70 externally of the penetrating channel 58 thereby reducing the possibility of tissue being snagged or stuck between the rod and the blade such that the blade can not be retracted. Passages 94 and 96 for endoscope 118 are arranged on opposite sides of the optical channel 50 but can be arranged anywhere within the endoscope tube as desired. Use of the modified endoscope 118 proceeds in essentially the same manner as previously described but with operating channel 120 functioning as a portal for passage of instruments, fluids, tissue and other objects through the endoscope. Moreover, since the operating channel 120 is straight, elongate instruments such as staplers or clip appliers, which are generally rigid, can be passed through the endoscope for performing functions within the body while being observed through the viewing port 40.

Figures 12, 13, 14, 15, 16:
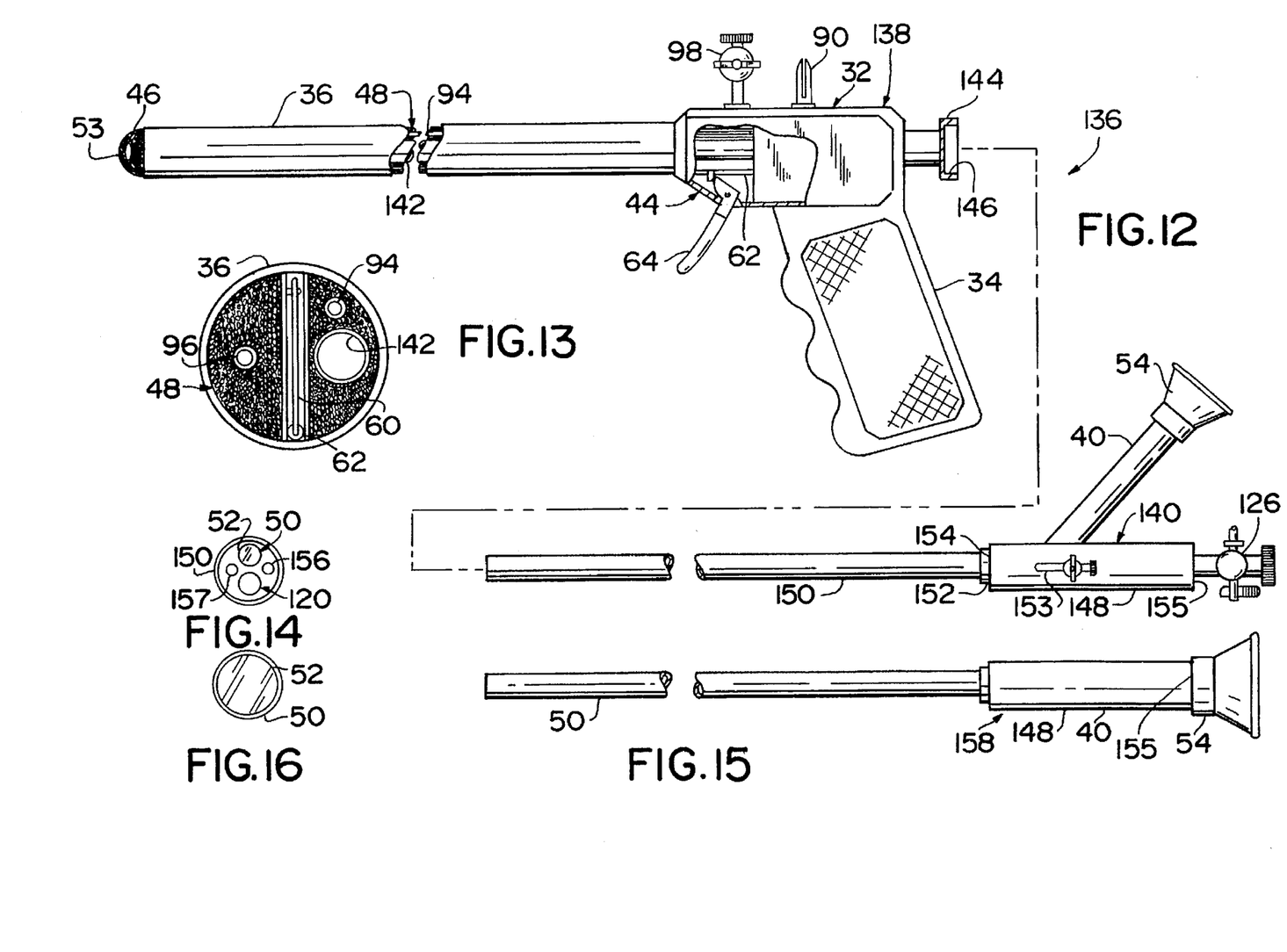
FIG. 12 is an exploded side view, partly in section, of another modified endoscope according to the present invention.
FIG. 13 is a front view of the modified endoscope of FIG. 12 taken along line 13—13.
FIG. 14 is a front view of the modified endoscope of FIG. 12 taken along line 14—14.
FIG. 15 is a broken side view of an alternative viewing unit for use with the endoscope of FIG. 12.
FIG. 16 is a front view of the alternate viewing unit of FIG. 15.

FIGS. 12-14 illustrate another modification of the endoscope of the present invention wherein the modified endoscope 136 includes separable illuminating and viewing units 138 and 140. Illuminating unit 138 is similar to endoscope 30 but without an optical channel 50 or a viewing port 40. Instead, a tubular sleeve 142 extends through housing 32 and endoscope tube 36 to define a portal through the endoscope where the optical channel would normally be positioned. A proximal end of the sleeve 142 carries a coupling 144 defining a cylindrical recess or socket 146.

Viewing unit 140 includes a cylindrical hub 148 and an elongate tubular shaft 150 extending distally from a mounting ring 152 surrounding an opening in the front wall 154 of the cylindrical hub 148. Optical and operating channels 50 and 120 extend longitudinally through the shaft 150. A proximal end of operating channel 120 extends through an opening in the rear wall 155 of cylindrical hub 148 and is coupled with a stopcock valve 126 to regulate passage of instruments through the operating channel. Another stopcock valve 153 is connected at the proximal end of one or more passages such as 156 or 157 disposed proximate optical window 52 primarily for controlling delivery of fluids such as lens cleaner to the optical window. The proximal end of optical channel 50 is coupled with a viewing port 40 that extends at an angle from a sidewall of the cylindrical hub 148 and terminates at eyepiece 54.

In use, the illuminating and viewing units 138 and 140 can be provided separately or in an assembled condition. If provided separately, the units can be assembled by inserting the shaft 150 of the viewing unit 140 into the sleeve 142 of the illuminating unit and advancing the shaft distally through the sleeve until the mounting ring 152 at the base of the shaft is seated within the cylindrical recess 146 of the coupling 144 carried at the proximal end of the sleeve. Shaft 150 is telescopically fitted within sleeve 142 and, together with coupling 144, the mating contact of the shaft with the sleeve maintains a gaseous seal along the length of the endoscope to prevent loss of pneumoperitoneum, for example, during endoscopic procedures.

Once assembled, the penetrating endoscope 136 is used in the manner previously described in connection with the endoscope 30 of FIG. 1; however, after the part of the procedure using the viewing capabilities of the endoscope is complete, the viewing unit 140 can be withdrawn from the illuminating unit 138 and another elongate implement such as a needle inserted through the sleeve 142, or the entire endoscope 136 including the illuminating and viewing units 138 and 140 can be withdrawn from the operative field simultaneously.

It will be appreciated that by forming the penetrating endoscope of separate illuminating and viewing units, the viewing unit can, for example, be fabricated using plastic optics to reduce cost and facilitate disposal after use. Although plastic optics are less expensive than their glass counterparts, conventional sterilization techniques can degrade the quality of the optics, making disposal of the viewing unit particularly advantageous. The illuminating unit is typically not adversely affected by sterilization and can therefore by made of suitable materials for being sterilized and reused.

FIGS. 15 and 16 illustrate a modified viewing unit 158 for use with the illuminating unit 138 of endoscope 136. Viewing unit 158 is similar to viewing unit 140 but with only an optical channel 50 disposed within the shaft and a colinear viewing port 40 extending proximally from the rear wall 155 of the cylindrical hub 148. The viewing unit 158 is advantageously used with illuminating unit 138 when there is no need for advancing implements through an operating channel. It can thus be made less expensively than viewing unit 140 to further facilitate disposal after use.

Figure 17:
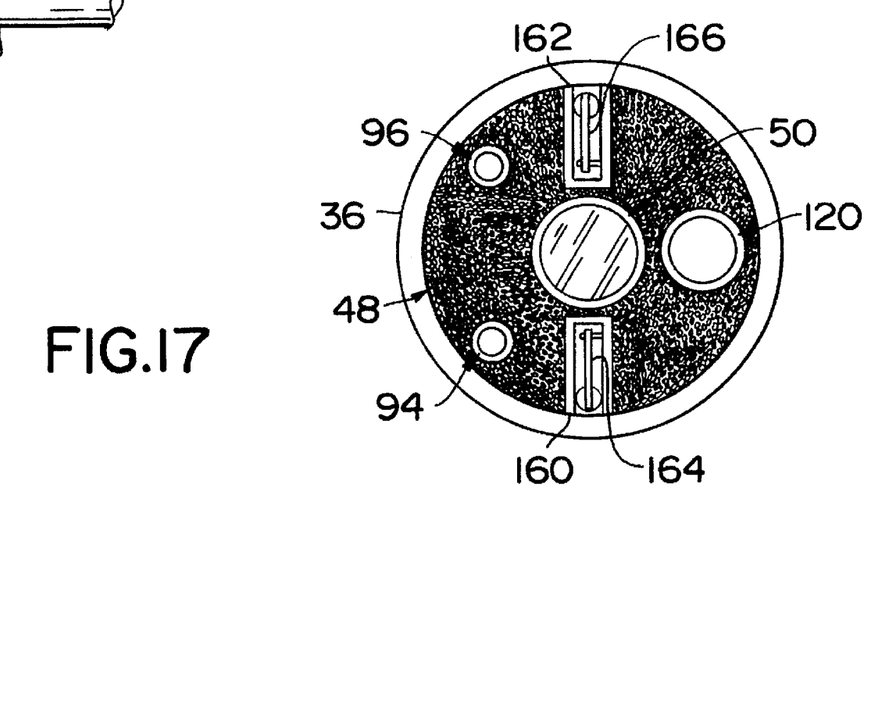
FIG. 17 is a front view of still another modification of an endoscope according to the present invention.

FIG. 17 illustrates a further modification of the penetrating endoscope of the present invention wherein a pair of penetrating channels 160 and 162 are arranged on opposite sides of a centrally located optical channel 50. Blades 164 and 166 for the modified endoscope are similar to blade 60 for endoscope 118 and are disposed within channels 160 and 162 for pivotal movement therein. The blades 164 and 166 of the modified endoscope can be operated separately or together using coupled rods, pulleys, cams or any other types of conventional linkages and are shown combined with an operating channel 120 and a pair of passages 94 and 96 disposed on the same side of the optical channel 50 opposite the operating channel 120.

A modification of the penetrating mechanism 44 for the endoscope of the present invention is shown in FIGS. 18A–21A and 18B–21B. The modification involves forming helical splines or threads 168 along the length of the control rod 62 distally of flange 80 for being threadedly engaged by a wall or partition 170 in the housing 32 (not shown) to create rotational movement of the rod as it is advanced distally by the trigger 64. Flange 80 has a notch or slot 172 formed in a peripheral edge of the flange and extending radially from the peripheral edge towards the rod. The slot 172 is configured to slide past the distally angled protrusion 84 of trigger 64 when the control rod 62 is rotated angularly a predetermined distance corresponding to a full distal extension of the penetrating member. When the slot 172 is rotated into alignment with the protrusion 84, the control rod flange 80 slides past the protrusion in a proximal direction under the influence of spring 78 (not shown).

Figures 18A, 18B:
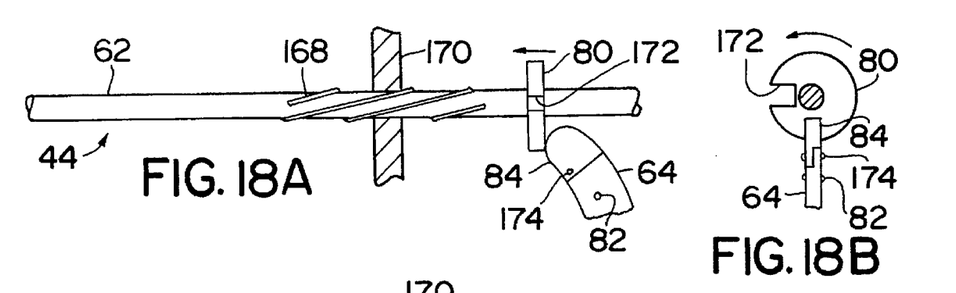

As best seen in FIGS. 18A and 18B, distal protrusion 84 is pivotally connected to trigger 64 by a pin 174 passing through the distal protrusion and the trigger. The pin 174 is located near a lower corner of the distal protrusion 84, looking at FIG. 18A, to permit counterclockwise rotation of the protrusion away from the trigger 64. A torsion spring or the like (not shown) biases the distal protrusion 84 in a clockwise direction looking at FIG. 18A; however, clockwise rotation is limited by mating contact of the distal protrusion 84 with the trigger 64.

Figure 19A:
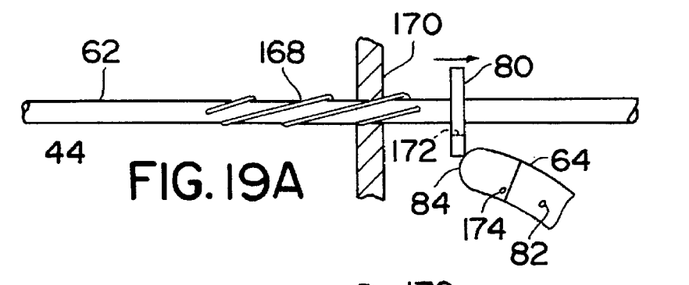
Figure 19B:
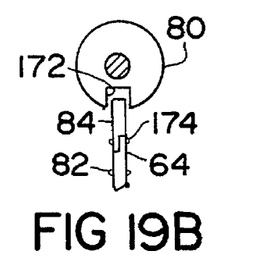
Figure 20A:
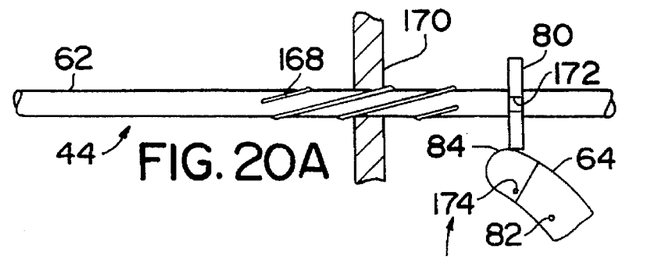
Figure 20B:
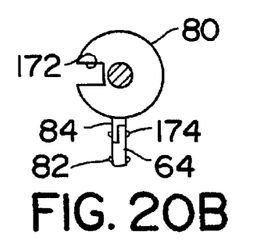
Figure 21A:
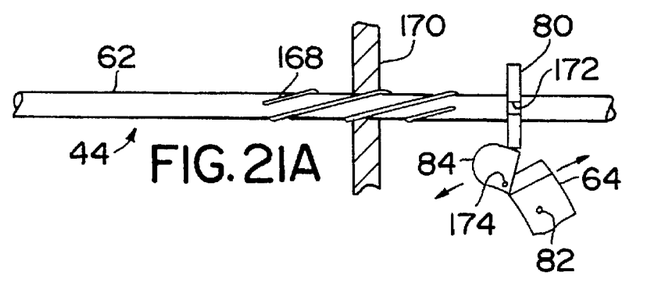
Figure 21B:
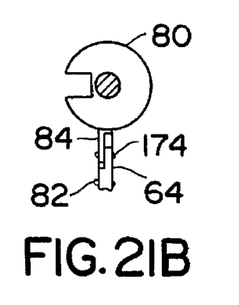

In operation, compression of the trigger 64 against handle 34 causes the trigger to rotate counterclockwise about pin 82 moving distal protrusion 84 into contact with flange 80 on the control rod 62 as shown in FIGS. 18A and 18B. Continued counterclockwise rotation of the trigger 64 urges the control rod 62 in a distal direction creating rotational movement of the rod as it passes through the threaded opening formed in wall 170 of the housing. When the rod is rotated angularly a predetermined distance corresponding to a full distal extension of the penetrating member, the notch 172 will be aligned with the distal protrusion 84 and will slide over the protrusion in a proximal direction under the influence of spring 78 as illustrated in FIGS. 19A and 19B. Trigger 64 is biased in a clockwise direction and will thus rotate back towards the flange 80 when released as shown in FIGS. 20A and 20B. Contact of the flange 80 with the proximal edge of the distal protrusion 84 causes the protrusion to rotate about pin 174 in a counterclockwise direction looking at FIG. 21A allowing the protrusion to slide underneath the flange as the trigger rotates clockwise and to return to the rest position shown in FIG. 1 when the protrusion reaches the proximal side of the flange and the torsion spring rotates the protrusion clockwise into mating engagement with the trigger.

Figure 22:
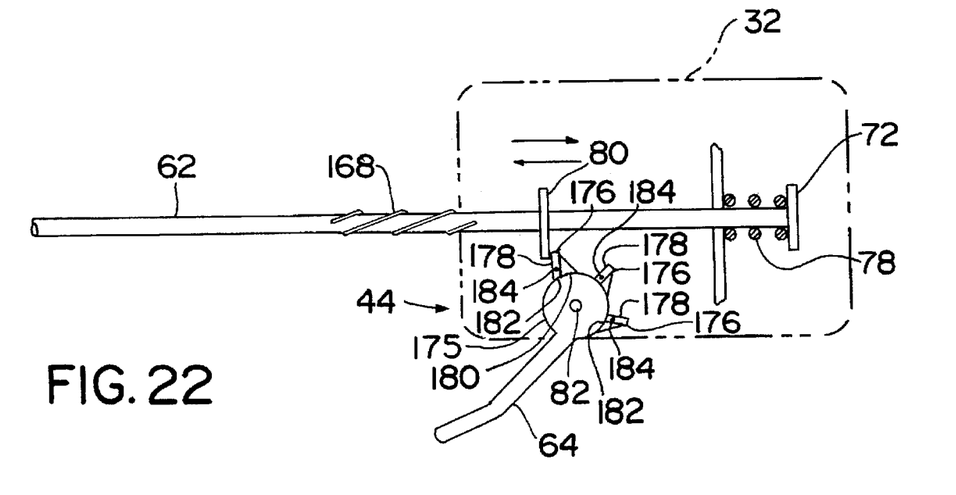
FIG. 22 is a fragmentary side view of a reciprocating trigger mechanism for the endoscope of the present invention.

FIG. 22 illustrates a further modification of the penetrating mechanism 44 wherein the upper or distal portion 175 of the trigger 64 is rounded and a plurality of ratcheting protrusions 176 are angularly spaced about the periphery of the rounded distal portion for successively engaging flange 80 on control rod 62. Ratcheting protrusions 176 are generally triangular and extend radially from rounded distal portion 175 to form surfaces 178 for engaging flange 80. A base 180 of each protrusion is normally seated against the peripheral edge of rounded distal portion 175. Lower distal corners 182 of the protrusions are pivotally mounted on the rounded distal portion 175 on pins 184 so that the protrusions can rotate about the pins to slide past the flange when the trigger is released as described above in connection with the distally-angled protrusion 84 illustrated in FIGS. 18A–21A and 18B–21B. In operation, the distalmost or first protrusion 176 is normally spaced proximally of the flange 80. Depression of the trigger 64 causes the distal portion 175 to rotate counterclockwise looking at FIG. 22 urging the first protrusion into engagement with flange 80.

The tangential force exerted by the flange 80 against the first protrusion does not cause clockwise rotation of the protrusion since the base 180 of the protrusion is seated on the peripheral edge of the distal portion 175 and the protrusion is hinged to allow only counterclockwise rotation from this position. The control rod 62 is thus driven distally by the protrusion to an extended position where the penetrating member carried by the rod is exposed. Continued depression of the trigger 64 causes the first protrusion to rotate beneath the flange 80 allowing spring 78 to retract the rod 62 until flange 80 is caught by the next protrusion in succession. Depending on the number of protrusions carried on the distal portion of the trigger, the penetrating member at the end of the control rod can be reciprocatingly moved from retracted to extended positions a number of times for each pull of the trigger. When the trigger 64 is released, protrusions 176 can rotate on pins 184 to pass under the flange 80 when returning to their original position spaced proximally of the flange.

Figure 23:
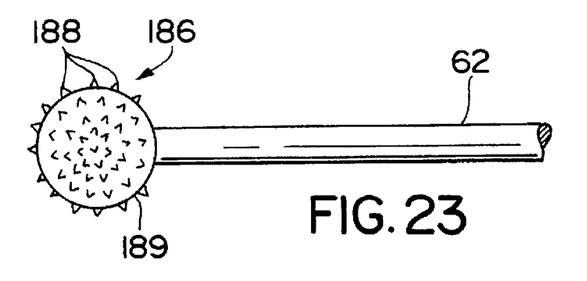
FIG. 23 is a fragmentary side view of an alternative penetrating member for the endoscope of the present invention.
Figure 24:
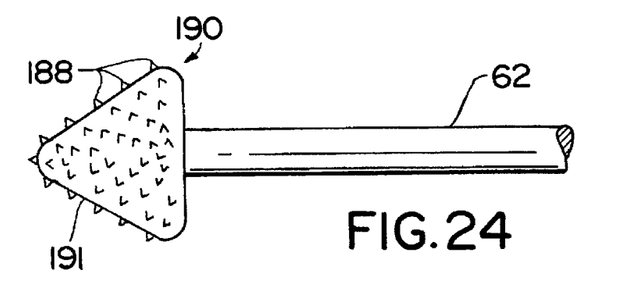
FIG. 24 is a fragmentary side view of another alternative penetrating member for the endoscope of the present invention.

FIGS. 23 and 24 illustrate alternative penetrating members for the endoscopes of the present invention. The penetrating member 186 shown in FIG. 23 is ball-shaped with a plurality of cutting members or burrs 188 arranged around the spherical surface 189 of the ball-shaped member. The penetrating member 190 shown in FIG. 24 is cone-shaped and includes a plurality of cutting members or burrs 188 arranged around the conical surface 191 of the member. Penetrating members 186 and 190 are each carried at the distal end of a control rod 62 and are particularly advantageous when driven by penetrating mechanisms which rotate the rods, such as the mechanism shown in FIGS. 18A through 21A.

Figure 25:
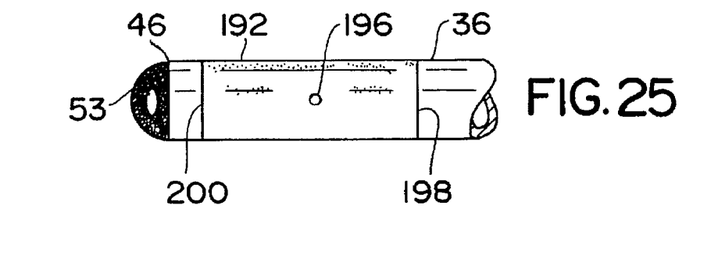
FIG. 25 is a fragmentary side view of a distal end of a modified endoscope according to the present invention.
Figure 26:
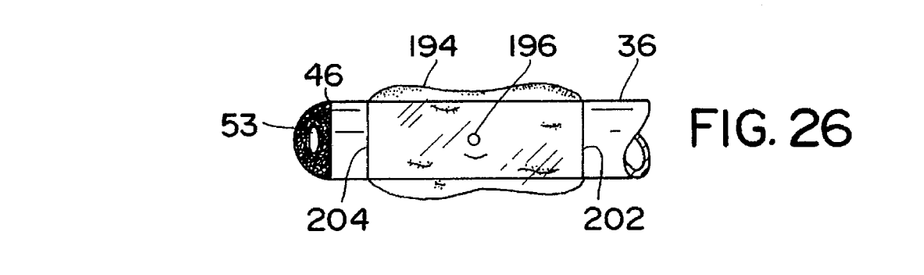
FIG. 26 is a fragmentary side view of a distal end of another modified endoscope according to the present invention.
Figure 27:
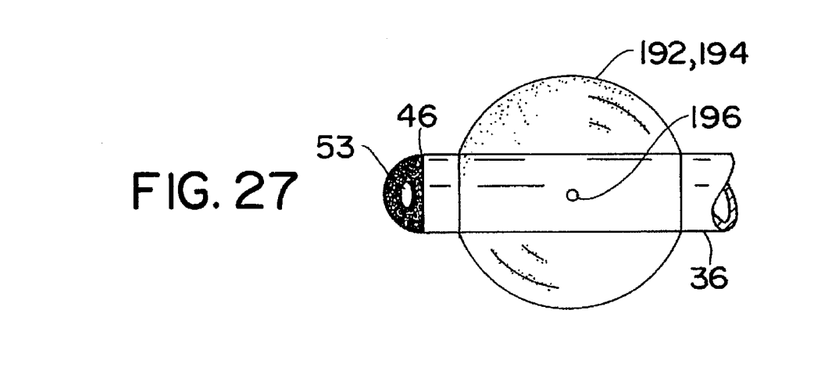
FIG. 27 is a fragmentary side view illustrating operation of either of the distal ends shown in FIGS. 25 and 26.

FIGS. 25 and 26 illustrate alternative distal end configurations for the endoscopes of the present invention, including inflatable membranes 192 and 194, respectively, and apertures 196 formed in the endoscope tube 36 beneath the membranes. Membrane 192 is elastic and surrounds the endoscope tube 36 in a snug fashion. The membrane 192 extends completely around the endoscope tube 36 and is sealed circumferentially at proximal and distal edges 198 and 200 to the endoscope tube 36. Membrane 194 is a flaccid, bag-like membrane which also completely surrounds the endoscopic tube 36 and is sealed circumferentially at proximal and distal edges 202 and 204 to the endoscopic tube 36. The inflatable membranes 192 and 194 can be used like balloons for creating spaces at locations within the body that are potential spaces between layered tissue or adjacent tissue structures, or non-existing spaces (i.e., within homogeneous tissue such as that found within the breast), as well as for expanding existing spaces (i.e., anatomical cavities). Inflation of the membranes 192 and 194 is accomplished by passing a fluid such as a gas through a passage or passages in the endoscope tube 36 and directing the fluid through the apertures 196 and into the membranes 192 and 194 to fill the membranes with the fluid as shown in FIG. 27. Passage of the fluid through the endoscope can be controlled by use of a stopcock valve or any other suitable valve mechanism.

Figure 28:
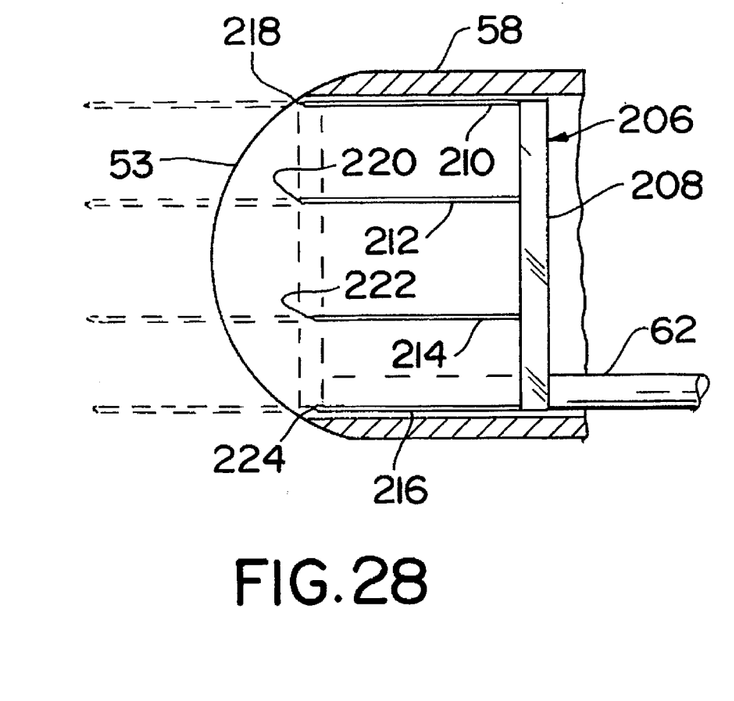
FIG. 28 is a fragmentary side view, partly in section, of yet another alternative penetrating member for the endoscope of the present invention.

FIG. 28 illustrates an alternative penetrating member for use with the endoscopes of the present invention. The penetrating member 206 is carried at the distal end of the control rod 62 and includes a base 208 extending perpendicularly from the control rod and four needles or prongs 210, 212, 214 and 216 extending transversely from the base 208 in a distal direction. Distal ends of the prongs form tissue penetrating tips 218, 220, 222 and 224 that are spaced proximally of the distal end of the penetrating channel 58 when the control rod is retracted. The needles 210, 212, 214 and 216 shown are all of the same length; however, it will be appreciated that needles of various lengths can be used, including needles having lengths that conform to the exterior profile of the blunt distal end of the endoscope.

The penetrating member 206 shown in FIG. 28 is advanced in the manner previously described for blade 60 but instead of rotating about a pivot, the penetrating member 206 protrudes linearly from the distal end 53 of the endoscope to penetrate anatomical tissue when extended as shown in phantom in FIG. 28. Penetration of the needles 210, 212, 214 and 216 into anatomical tissue creates a linear perforation or line of weakening in the tissue, allowing the blunt distal end 53 of the endoscope to be pressed against the perforated tissue when the needles are retracted in order to create an opening for passage of the endoscope. Use of needles as penetrating members is particularly advantageous when encountering adhesions within the body. For example, in the case of a dense bowel adhesion with the peritoneum, the bowel wall can be separated from the peritoneum by extending the needles from the endoscope to perforate the adhered tissue, retracting the needles into the endoscope and pushing between the bowel wall and the peritoneum with the blunt distal end of the endoscope. Use of needles for this purpose is preferred to blades since perforation of the serous layer lining the bowel wall is less likely to cause leakage of the bowel contents.

Once within anatomical tissue or a cavity, the endoscopes of the present invention can be used for dissecting a portion of the tissue penetrated, or a mass or lump disposed within the tissue, by extending the penetrating member to cut into the tissue, mass or lump, and twisting the endoscope about the longitudinal axis of the scope to dislodge a sample. Alternatively, or in addition to twisting the endoscope, multiple intersecting or nonintersecting cuts can be made in the tissue, mass or lump to separate a sample. One of the passages 94 and 96 or an operating channel 120 can then be used for creating suction to capture or collect the sample.

Also, when placed in anatomical tissue, the endoscope of the present invention can be tilted to raise the tissue, creating a tent-like effect, for easing penetration of other members into the space occupied by the endoscope. Under some circumstances the illumination from the distal end of the endoscope will be visible externally of the raised tissue providing a guide for insertion of other penetrating members or instruments.

From the above, it will be appreciated that the endoscope of the present invention can be used for penetrating anatomical tissue, transmitting fluids to and from locations within the body, collecting tissue samples, expanding potential, non-existing or existing spaces within the body, and manipulating anatomical tissue, as well as for illuminating and viewing before, during and after any of the above functions are performed. The endoscope can be formed with any number of penetrating channels having any suitable configuration for accommodating one or more penetrating members. By "penetrating member" is meant any member that can cut, puncture, perforate or otherwise separate or remove anatomical tissue. When the penetrating members are blades, the blades can be generally flat single-edge blades as shown or have any other configuration suitable for cutting anatomical tissue including curved, angled, serrated and/or toothed cutting edges. When needles are used as penetrating members, any number of needles having the same or different lengths can be mounted on a base and carried by a single control rod or plural control rods as desired. Although a rod is shown for controlling movement of the penetrating members, other mechanisms can be used, including but not limited to flexible linkages, cams and pulleys.

Any number of passages can be arranged within the endoscope tube to define openings proximate the optical window or penetrating channel for transmission of fluids and tissue. Furthermore, any number of operating channels can be arranged within the endoscope tube to permit passage of medical instruments, fluids, tissue and other objects through the endoscope. The passages and operating channels can have any configuration in cross-section and can be rigid or flexible and straight or angled as desired.

The components of the endoscope of the present invention can be fabricated using any suitable medically-acceptable materials and can be made disposable for single-patient use or in a manner to be sterilized for re-use. The optical elements can include glass or plastic lenses, charge coupled devices, rigid rods and/or optical fibers in any conventional configuration. Similarly, any known illumination and viewing systems for endoscopes can be used, including direct viewing systems and those employing television displays. Further, the endoscope can be utilized with or without a portal sleeve or cannula for gaining access to locations and tissue within the body.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An endoscope comprising
    an endoscope tube;
    an illumination system disposed within said endoscope tube;
    a viewing system disposed within said endoscope tube and including a viewing window at a distal end;
    a penetrating member disposed at least partly within said endoscope tube and having a distal end for penetrating anatomical tissue, wherein said endoscope tube, illumination system and viewing system cooperate to define a blunt distal end of said endoscope with a smooth, rounded configuration and said penetrating member is movable between a retracted position where said distal end of said penetrating member is proximally spaced from said blunt distal end of said endoscope to permit non-traumatic tissue contact with said blunt distal end and an extended position where said distal end of said penetrating member protrudes beyond said blunt distal end of said endoscope to penetrate anatomical tissue, said penetrating member being laterally offset from said viewing window in said retracted position; and
    a control mechanism coupled with said penetrating member, said control mechanism being selectively operable to move said penetrating member between said retracted and extended positions.

2. An endoscope as recited in claim 1 wherein said viewing system includes an optical channel extending along a central longitudinal axis of said endoscope tube in spaced relation thereto to define an annular region around the optical channel and wherein said penetrating member is disposed within said annular region between said optical channel and said endoscope tube in said retracted position.

3. An endoscope as recited in claim 2 wherein said penetrating member is oriented radially within said annular region.

4. An endoscope as recited in claim 1 wherein said viewing system includes an optical channel extending along an eccentric longitudinal axis of said endoscope tube and said penetrating member extends diametrically across said endoscope tube.

5. An endoscope as recited in claim 1 wherein said viewing system is disposed within an optical channel extending along an eccentric longitudinal axis of said endoscope tube and said penetrating member is disposed within a plane containing said eccentric longitudinal axis.

6. An endoscope as recited in claim 1 and further comprising an operating channel disposed within said endoscope tube to define a portal suitable for passage of medical instruments.

7. An endoscope as recited in claim 1 wherein said viewing system includes an optical channel and further comprising at least one passage defining an opening at said distal end of said endoscope proximate said optical channel for transmitting fluids.

8. An endoscope as recited in claim 1 wherein said penetrating member is a blade having a distal cutting edge.

9. An endoscope as recited in claim 8 wherein said blade is disposed within a penetrating channel extending through said endoscope tube.

10. An endoscope as recited in claim 8 wherein said blade is flat and said cutting edge conforms to said blunt distal end of said endoscope when retracted.

11. An endoscope as recited in claim 1 wherein said penetrating member includes a plurality of needles.

12. An endoscope as recited in claim 11 wherein said needles are parallel and spaced diametrically across said endoscope tube.

13. An endoscope as recited in claim 12 wherein tissue penetrating tips of said needles conform to said blunt distal end of said endoscope when retracted.

14. An endoscope as recited in claim 1 wherein said viewing system is disposed within an optical channel and further comprising a housing mounting said endoscope tube and a hub mounting said optical channel, said hub being configured to mate with said housing in a removable manner.

15. An endoscope as recited in claim 1 wherein said control mechanism includes a rod disposed within said endoscope tube and an advancing mechanism coupled with said rod to move said rod distally, said penetrating member being mounted at a distal end of said rod.

16. An endoscope as recited in claim 1 and further comprising an inflatable membrane mounted at a distal end of said endoscope tube and means for inflating said membrane.

17. An endoscope as recited in claim 1 wherein said penetrating member includes a burr.

18. An endoscope as recited in claim 7 wherein said control mechanism includes a mechanism to rotate said burr.

19. An endoscope comprising
    an endoscope tube;
    an illumination system disposed within said endoscope tube;
    viewing system disposed within said endoscope tube;
    a penetrating member disposed at least partly within said endoscope tube and having a distal end for penetrating anatomical tissue, wherein said endoscope tube, illumination system and viewing system cooperate to define a blunt distal end of said endoscope with a smooth, rounded configuration and said penetrating member is movable between a retracted position where said distal end of said penetrating member is proximally spaced from said blunt distal end of said endoscope to permit non-traumatic tissue contact with said blunt distal end and an extended position where said distal end of said penetrating member protrudes beyond said blunt distal end of said endoscope to penetrate anatomical tissue; and
    a control mechanism coupled with said penetrating member, said control mechanism being selectively operable to move said penetrating member between said retracted and extended positions;
    wherein said viewing system includes an optical channel extending along a central longitudinal axis of said endoscope tube in spaced relation thereto to define an annular region around the optical channel and wherein said penetrating member is disposed within said annular region between said optical channel and said endoscope tube in said retracted position; and wherein said penetrating member includes a plurality of spaced tissue penetrating members on opposite sides of said optical channel and a curved portion wrapping around said optical channel to connect said tissue penetrating members.

20. An endoscope comprising an endoscope tube;

an illumination system disposed within said endoscope tube;

a viewing system disposed within said endoscope tube;

a penetrating member disposed at least partly within said endoscope tube and having a distal end for penetrating anatomical tissue, wherein said endoscope tube, illumination system and viewing system cooperate to define a blunt distal end of said endoscope with a smooth, rounded configuration and said penetrating member is movable between a retracted position where said distal end of said penetrating member is proximally spaced from said blunt distal end of said endoscope to permit non-traumatic tissue contact with said blunt distal end and an extended position where said distal end of said penetrating member protrudes beyond said blunt distal end of said endoscope to penetrate anatomical tissue; and a control mechanism coupled with said penetrating member, said control mechanism being selectively operable to move said penetrating member between said retracted and extended positions;

wherein said penetrating member includes a blade having a distal cutting edge, said blade being disposed within a penetrating channel extending through said endoscope tube; and wherein one end of said blade is pivotally connected to said penetrating channel and an opposed end of said blade is coupled with said control mechanism to induce rotation of said blade about said pivoted end.

21. An endoscope comprising an endoscope tube;

an illumination system disposed within said endoscope tube;

a viewing system disposed within said endoscope tube;

a penetrating member disposed at least partly within said endoscope tube and having a distal end for penetrating anatomical tissue, wherein said endoscope tube, illumination system and viewing system cooperate to define a blunt distal end of said endoscope with a smooth, rounded configuration and said penetrating member is movable between a retracted position where said distal end of said penetrating member is proximally spaced from said blunt distal end of said endoscope to permit non-traumatic tissue contact with said blunt distal end and an extended position where said distal end of said penetrating member protrudes beyond said blunt distal end of said endoscope to penetrate anatomical tissue; and a control mechanism coupled with said penetrating member, said control mechanism being selectively operable to move said penetrating member between said retracted and extended positions;

wherein said penetrating member includes a blade having a distal cutting edge and said cutting edge of said blade includes a plurality of teeth.

22. An endoscope comprising:

an endoscope tube;

an illumination system disposed within said endoscope tube;

a viewing system including an optical channel disposed within said endoscope tube;

a penetrating member disposed at least partly within said endoscope tube and having a distal end for penetrating anatomical tissue, wherein said endoscope tube illumination system and viewing system cooperate to define a blunt distal end of said endoscope with a smooth, rounded configuration and said penetrating member is movable between a retracted position where said distal end of said penetrating member is proximally spaced from said blunt end to permit non-traumatic tissue contact with said blunt end and an extended position where said distal end of said penetrating member protrudes beyond said blunt distal end of said endoscope to penetrate anatomical tissue; and a control mechanism coupled with said penetrating member, said control mechanism being selectively operable to move said penetrating member between said retracted and extended positions;

a housing mounting said endoscope tube;

a hub mounting said optical channel and having a configuration to mate with said housing in a removable manner; and an operating channel mounted by said hub next to said optical channel, wherein said distal end of said endoscope includes an opening and said operating channel communicates with said opening when said hub is mated with said housing.

23. An endoscope comprising an endoscope tube;

an illumination system disposed within said endoscope tube;

a viewing system disposed within said endoscope tube;

a penetrating member disposed at least partly within said endoscope tube and having a distal end for penetrating anatomical tissue, wherein said endoscope tube, illumination system and viewing system cooperate to define a blunt distal end of said endoscope with a smooth, rounded configuration and said penetrating member is movable between a retracted position where said distal end of said penetrating member is proximally spaced from said blunt distal end of said endoscope to permit non-traumatic tissue contact with said blunt distal end and an extended position where said distal end of said penetrating member protrudes beyond said blunt distal end of said endoscope to penetrate anatomical tissue;

a control mechanism coupled with said penetrating member, said control mechanism being selectively operable to move said penetrating member between said retracted and extended positions, wherein said control mechanism includes a rod disposed within said endoscope tube and an advancing mechanism coupled with said rod to move said rod distally, said penetrating member being mounted at a distal end of said rod; and a housing mounting a proximal end of said endoscope tube, wherein said advancing mechanism includes a flange carried on said rod within said housing and a trigger pivotally mounted by said housing to engage said flange.

24. An endoscope as recited in claim 23 wherein said penetrating member is pivoted at one end and pivotally connected to said rod at an opposite end, whereby distal movement of said rod causes said penetrating member to rotate about said pivoted end exposing a distal end of said penetrating member.

25. An endoscope as recited in claim 24 and further comprising a retracting mechanism cooperating with said advancing mechanism to automatically retract said penetrating member after said penetrating member reaches said extended position.

26. An endoscope as recited in claim 25 wherein said retracting mechanism includes bias means for biasing said rod proximally toward said retracted position.

27. An endoscope as recited in claim 26 wherein said retracting mechanism further includes helical splines formed on said rod to induce rotation of said rod relative to a wall of said housing and a notch formed in said flange to slide over said trigger when said rod has rotated a predetermined angular amount corresponding to said extended position.

28. An endoscope as recited in claim 27 wherein said trigger includes means for inducing reciprocating movement of said penetrating member.

29. An endoscope as recited in claim 28 wherein said reciprocating means includes a plurality of ratcheting protrusions at a terminal end of said trigger proximate said flange.

* * * * *